United States Patent [19]
Amasino et al.

[11] Patent Number: 5,689,042
[45] Date of Patent: Nov. 18, 1997

[54] TRANSGENIC PLANTS WITH ALTERED SENESCENCE CHARACTERISTICS

[75] Inventors: Richard M. Amasino; Susheng Gan, both of Madison, Wis.

[73] Assignee: Wisconsin Alumni Research Foundation, Madison, Wis.

[21] Appl. No.: 413,135

[22] Filed: Mar. 29, 1995

[51] Int. Cl.$^6$ .............................. A01H 5/00; A01H 5/10; C12N 15/29; C12N 15/82; C12N 5/04
[52] U.S. Cl. .................. 800/205; 536/23.2; 536/24.1; 435/69.1; 435/70.1; 435/172.3; 435/193; 435/240.4; 800/250; 800/255
[58] Field of Search .............................. 536/23.2, 24.1; 435/69.1, 70.1, 172.3, 240.4, 193; 800/205, 250, 255

[56] References Cited

U.S. PATENT DOCUMENTS 5,177,307  1/1993  Houck et al. ........................ 800/205

OTHER PUBLICATIONS

Chory et al. 1994. Plant Physiol. 104(2): 339–347.
Bernhard et al. 1994. Plant Science 98(1): 7–14.
Hensel et al. 1993. Plant Cell 5(5): 553–564.
Levin, R. 1987. Science 237:1570.
Reeck et al. 1987. Cell 50:667.
Ainley, W.M., et al., "Regulatable Endogenous Production of Cytokinins up to 'Toxic' Levels in Transgenic Plants and Plant Tissues," *Plant Mol. Biol.*, 22:13–23 (1993).
Li, Y., et al., "Altered Morphology in Transgenic Tobacco Plants That Overproduce Cytokinins in Specific Tissues and Organs," *Dev. Biol.*, 153:386–395 (1992).
Lohman, K.N., et al., "Molecular analysis of natural leaf senescence in Arabidopsis thaliana," *Phys. plantarum*, 92:322–328 (1994).

Martineau, B., "Fruit–Specific Expression of the A. tumefaciens Isopentenyl Transferase Gene in Tomato: Effects on Fruit Ripening and Defense–Related Gene expression in Leaves," *The Plant Journal*, 5:11–19 (1994).
Medford, J.I., et al., "Alterations of Endogenous Cytokinins in Transgenic Plants Using a Chimeric Isopentenyl Transferase Gene," *The Plant Cell*, 1:403–413 (1989).
Ooms, G., et al., "Phenotypic Changes in T–cyt–Transformed Potato Plants are Consistent with Enhanced Sensitivity of Specific Cell Types to Normal Regulation by Root–Derived Cytokinin," *Plant Mol. Biol.*, 17:727–743 (1991).
Smart, C.M., et al., "Delayed Leaf Senescence in Tobacco Plants Transformed with tmr, a Gene for Cytokinin Production in Agrobacterium," *The Plant Cell*, 3:647–656 (1991).
Smigocki, A.C., "Cytokinin Content and Tissue Distribution in Plants Transformed by a Reconstructed Isopentenyl Transferase Gene," *Plant Mol. Biol.*, 16:105–115 (1991).
Staden, J.V., et al., "Cytokinins and Senescence," Chapter 9 in *Senescence and Aging in Plants*, Academic Press, Inc. (1988).
Van Loven, K., et al., "Morphometric Analysis of the Growth of Phsp70–ipt Transgenic Tobacco Plants," *J. Exp. Botany*, 44:1671–1678 (1993).

*Primary Examiner*—David T. Fox
*Attorney, Agent, or Firm*—Quarles & Brady

[57] ABSTRACT

A genetic construct comprising an SAG12 promoter sequence operably connected to a protein-coding DNA sequence not natively connected to the promoter sequence is disclosed. Preferably, this SAG12 promoter sequence is the first 602 bp of SEQ ID NO:2 and the protein-coding sequence encodes isopentenyl transferase.

24 Claims, 3 Drawing Sheets

▼a -2073 bp EcoR V
```
GATATCTCTT TTTATATTCA AACAATAAGT TGAGATATGT TTGAGAAGAG GACAACTATT
CTCGTGGAGC ACCGAGTCTG TTTTATATTA GAAACCCGAT TGTTATTTTT AGACTGAGAC
AAAAAAGTAA AATCGTTGAT TGTTAAAATT TAAAATTAGT TTCATCACGT TTCGATAAAA
AAATGATTAG TTATCATAGC TAATATAGCA TGATTCTAAA TTTGTTTTTT GACACCCTTT
TTTTCTCTCT TTGGTGTTTT CTTAACATTA GAAGAACCCA TAACAATGTA CGTTCAAATT
AATTAAAAAC AATATTTCCA AGTTTTATAT ACGAAACTTG TTTTTTTAAT GAAAACAGTT
GAATAGTTGA TTATGAATTA GTTAGATCAA TACTCAATAT ATGATCAATG ATGTATATAT
ATGAACTCAG TTGTTATACA AGAAATGAAA ATGCTATTTA AATACCGATC ATGAAGTGTT
AAAAAGTGTC AGAATATGAC ATGAAGCGTT TTGTCCTACC GGGTATCGAG TTATAGGTTT
GGATCTCTCA AGAATATTTT GGGCCATATT AGTTATATTT GGGCTTAAGC GTTTTGCAAA
GAGACGAGGA AGAAAGATTG GGTCAAGTTA ACAAAACAGA GACACTCGTA TTAGTTGGTA
CTTTGGTAGC AAGTCGATTT ATTTGCCAGT AAAAACTTGG TACACAACTG ACAACTCGTA
TCGTTATTAG TTTGTACTTG GTACCTTTGG TTAAGAAAAA GTTGATATAG TTAAATCAGT
TGTGTTCATG AGGTGATTGT GATTTAATTT GTTGACTAGG GCGATTCCTT CACATCACAA
TAACAAAGTT TTATAGATTT TTTTTTATAA CATTTTTGCC ACGCTTCGTA AAGTTTGGTA
TTTACACCGC ATTTTTCCCT GTACAAGAAT TCATATATTA TTTATTTATA TACTCCAGTT
GACAATTATA AGTTTATAAC GTTTTTACAA TTATTTAAAT ACCATGTGAA GATCCAAGAA
TATGTCTTAC TTCTTCTTTG TGTAAGAAAA CTAACTATAT CACTATAATA AAATAATTCT
AATCATTATA TTTGTAAATA TGCAGTTATT TGTCAATTTT GAATTTAGTA TTTTAGACGG
TTATCACTTC AGCCAAATAT GATTTGGATT TAAGTCCAAA ATGCAATTTC GTACGTATCC
CTCTTGTCGT CTAATGATTA TTTCAATATT TCTTATATTA TCCCTAACTA CAGAGCTACA
TTTATATTGT ATTCTAATGA CAGGGAAACT TTCATAGAGA TTCAGATAGA TGAAATTGGT
GGGAAACATC ATTGAACAGG AAACTTTTAG CAAATCATAT CGATTTATCT ACAAAAGAAT
ACTTAGCGTA ATGAAGTTCA CTTGTTGTGA ATGACTATGA TTTGATCAAA TTAGTTAATT
```
▼b -602 bp Hind III
```
TTGTCGAATC ATTTTTCTTT TTGATTTGAT TAAGCTTTTA ACTTGCACGA ATGGTTCTCT
TGTGAATAAA CAGAATCTTT GAATTCAAAC TATTTGATTA GTGAAAAGAC AAAAGAAGAT
TCCTTGTTTT TATGTGATTA GTGATTTTGA TGCATGAAAG GTACCTACGT ACTACAAGAA
AAATAAACAT GTACGTAACT ACGTATCAGC ATGTAAAAGT ATTTTTTTCC AAATAATTTA
TACTCATGAT AGATTTTTTT TTTTGAAAT GTCAATTAAA AATGCTTTCT TAAATATTAA
TTTTAATTAA TTAAATAAGG AAATATATTT ATGCAAAACA TCATCAACAC ATATCCAACT
TCGAAAATCT CTATAGTACA CAAGTAGAGA AAATAAATTT TACTAGATAC AAACTTCCTA
ATCATCAATT ATAAATGTTT ACAAAACTAA TTAAACCCAC CACTAAAATT AACTAAAAAT
CCGAGCAAAG TGAGTGAACA AGACTTGATT TCAGGTTGAT GTAGGACTAA AATGGCTACG
TATCAAACAT CAACGATCAT TTAGTTATGT ATGAATGAAT GTAGTCATTA CTTGTAAAAC
```
-1 ▼+1
```
AAAAATGCTT TGATTTGGAT CAATCACTTC ATGTGAACAT TAGCAATTAC ATCAACCTTA
TTTTCACTAT AAAACCCCAT CTCAGTACCC TTCTGAAGTA ATCAAATTAA GAGCAAAAGT
```
▼ Nco I —>IPT
```
CATTTAACTT TCCTAAAACC ATGGACCCTG CATCTAATTT TCGGTCCAAC TTGCACAGGA
AAGACGACGA CCGCGATAGC TCTTGCCCAG CAGACAGGGC TTCCAGTCCT TTCGCTTGAT
CGGGTCCAAT GCTGTCCTCA ACTATCAACC GGAAGCGGAC GACCAACAGT GGAAGAACTG
AAAGGAACGA CGCGTCTCTA CCTTGATGAT CGGCCTCTGG TGGAGGGTAT CATCGCAGCC
AAGCAAGCTC ATCATAGGCT GATCGAGGAG GTGTATAATC ATGAGGCCAA CGGCGGGCTT
ATTCTTGAGG GAGGATCCAC CTCGTTGCTC AACTGCATGG CGCGAAACAG CTATTGGAGT
GCAGATTTTC GTTGGCATAT TATTCGCCAC AAGTTACCCG ACCAAGAGAC CTTCATGAAA
GCGGCCAAGG CCAGAGTTAA GCAGATGTTG CACCCCGCTG CAGGCCATTC TATTATTCAA
GAGTTGGTTT ATCTTTGGAA TGAACCTCGG CTGAGGCCCA TTCTGAAAGA GATCGATGGA
TATCGATATG CCATGTTGTT TGCTAGCCAG AACCAGATCA CGGCAGATAT GCTATTGCAG
CTTGACGCAA ATATGGAAGG TAAGTTGATT AATGGGATCG CTCAGGAGTA TTTCATCCAT
GCGCGCCAAC AGGAACAGAA ATTCCCCCAA GTTAACGCAG CCGCTTTCGA CGGATTCGAA
```
▼ Sst I —>NOS-ter
```
GGTCATCCGT TCGGAATGTA TTAGGTTACG CCAGCCCTGA GCTCGATCGT TCAAACATTT
GGCAATAAAG TTTCTTAAGA TTGAATCCTG TTGCCGGTCT TGCGATGATT ATCATATAAT
TTCTGTTGAA TTACGTTAAG CATGTAATAA TTAACATGTA ATGCATGACG TTATTTATGA
GATGGGTTTT TATGATTAGA GTCCCGCAAT TATACATTTA ATACGCGATA GAAAACAAAA
TATGGCGCGC AAACTGGGAT AAATTATCGC GCGCGGTGTC ATCTATGTTA CTAGATCGAA
TTC
```

TRANSGENIC PLANTS WITH ALTERED SENESCENCE CHARACTERISTICS

STATEMENT REGARDING FEDERALLY-SPONSORED RESEARCH

This invention was made with United States Government support awarded by NSF, Grant #NSF PRESIDENTIAL YOUNG INVESTIGATOR AWARD TO RICHARD M. AMASINO, #8957036. The United States Government has certain rights in this invention.

FIELD OF THE INVENTION

In general, the present invention relates to the field of plant molecular biology. Specifically, the present invention relates to transgenic plants with inserted transgenes that are activated by development-specific promoters.

BACKGROUND

Leaf senescence is a phase of development during which cells undergo distinct metabolic and structural changes prior to cell death (Noodén, *Senescence and Aging in Plants*, (L. D. Noodén and A. C. Leopold, Ed.), pp. 391–439, Academic Press, San Diego, Calif., 1988). It is an important phase in the plant life cycle that is thought to contribute to fitness by recycling nutrients to actively growing regions. The initiation of leaf senescence can be induced by a variety of external factors such as shading, mineral deficiency, drought and pathogen infection (Thomas, et al., *Ann. Rev. Plant Physiol.* 31:83–111, 1980) and by developmental processes such as seed development (Noodén, 1988, supra). In the absence of such factors, leaf senescence occurs in an age-dependent manner in many species (Batt, et al., *J. Exp. Bot.* 26:569–579, 1975; Hensel, et al., *Plant Cell* 5:553–564, 1993; Jiang, et al., *Plant Physiol.* 101:105–112, 1993).

Physiological and genetic studies indicate that senescence is a highly regulated process (Noodén, 1988, supra; Thomas, 1980, supra). The progression of a leaf through the senescence program is visibly marked by the loss of chlorophyll and consequent yellowing, a result of the disassembly of the chloroplast (Thomson, et al., *Plant Senescence: Its Biochemistry and Physiology*, pp. 20–30, 1987; Woolhouse, *Can. J. Bot.* 62:2934–2942, 1984). Leaf senescence involves degradation of proteins, nucleic acids and membranes, and the subsequent transport of the nutrients resulting from this degradation to other regions of the plant, such as developing seeds, leaves, or storage organs (Noodén, 1988, supra; Woolhouse, 1984, supra).

Molecular studies indicate that changes in gene expression are associated with the senescence program. The levels of mRNAs encoding proteins involved in photosynthesis decrease during senescence (Bate, et al., *J. Exp. Bot.* 42:801–811, 1991; Hensel, et al., *Plant Cell* 5:553–564, 1993; Jiang, et al., *Plant Physiol.* 101:105–112, 1993), while mRNA levels of genes encoding proteins thought to be involved in the senescence program increase (Graham, et al., *Plant Cell* 4:349–357, 1992, Hensel, et al., *Plant Cell* 5:553–564, 1993; Kamachi, et al., *Plant Physiol.* 93:1323–1329, 1992; Taylor, et al., *Proc. Natl. Acad. Sci. USA* 90:5118–5122, 1993). The activities of several enzymes that are likely to play a role in the breakdown and mobilization of nutrients have also been shown to increase during senescence (Blank, et al., *Plant Physiol.* 97:1409–1413, 1991) Debellis, et al., *Plant Cell. Physiol.* 32:1227–1235, 1991; Friedrich, et al., *Plant Physiol.* 65:1103–1107, 1980; Pistelli, et al., *J. Plant Physiol.* 19:723–729, 1992).

Although the general changes that occur during senescence are known, many of the biochemical details of how nutrient remobilization occurs remain to be determined. Furthermore, little is understood of how the changes in gene expression that accompany senescence are regulated.

Promoters capable of promoting gene expression during the plant developmental stage of senescence are needed in the art of plant molecular biology.

As a first step towards obtaining this goal, we investigated macromolecular changes that occur during leaf senescence in *Arabidopsis thaliana*. The onset of leaf senescence in Arabidopsis is determined by leaf age (Hensel, et al., supra). This predictability of the senescence program in Arabidopsis facilitated an integrated study of changes in RNA, chlorophyll, protein, and gene expression associated with natural leaf senescence in the intact plant. We also used this system, as recited here, to isolate and characterize the temporal expression patterns of mRNAs that increase and decrease in abundance during leaf senescence. These senescence-specific mRNAs allowed us, as described below, to isolate and characterize novel senescence-specific promoters.

SUMMARY OF THE INVENTION

The present invention is a genetic construct comprising an SAG12 promoter sequence operably connected to a protein-coding DNA sequence not natively connected to the promoter sequence. Preferably, the SAG12 promoter sequence is the SAG12-1 sequence. Most preferably, the SAG12 promoter is the first 602 bp of SEQ ID NO:2 and the protein-coding DNA sequence encodes isopentenyl transferase.

The present invention is also a cell or a plant containing the genetic construct.

It is an object of the present invention to provide a genetic construct with a promoter sequence enabling senescence-specific gene expression operably linked to a protein-coding sequence.

It is another object of the present invention to provide a senescence-specific promoter linked to a sequence encoding an enzyme that catalyzes the synthesis of a plant hormone, preferably cytokinin.

It is another object of the present invention to provide a senescence-specific promoter linked to an isopentenyl transferase sequence.

It is another object of the present invention to provide a transgenic plant that contains a transgene expressed only in senescing tissue.

It is a feature of the present invention that gene expression can be targeted specifically to senescing tissue, thus avoiding constitutive expression that could be damaging.

Other objects, advantages, and features of the present invention will become apparent after review of the specification, drawings, and claims.

DESCRIPTION OF THE DRAWINGS

FIG. 3 is the nucleotide sequence of SAG12-1 promoter/IPT/NOS-ter construct. The "a" and "b" labels correspond to "a" and "b" in FIGS. 1 and 2.

DETAILED DESCRIPTION OF THE INVENTION

Figure 1:
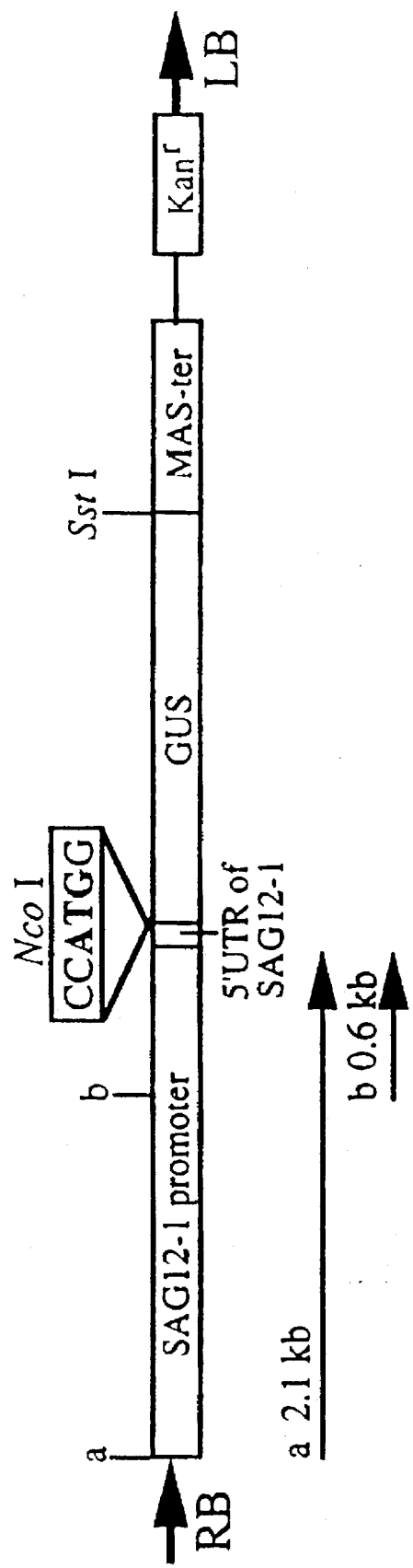
FIG. 1 is a schematic map of SAG12-1 promoter/GUS/MAS-ter construct in a binary vector.

One aspect of the present invention is a genetic construct comprising a senescence-specific promoter operably linked to a foreign gene sequence that is not natively associated with the promoter. A useful senescence-specific promoter, identified here as the SAG12 promoter, has been characterized. The availability of a senescence-specific promoter has also enabled the creation of transgenic plants with altered senescence morphology, e.g. delayed senescence. This finding offers a mechanism to extend the growth of useful plants.

Isolation of a particular SAG12 promoter from *Arabidopsis thaliana*, SAG12-1, is described in detail below. Basically, a senescence-specific cDNA, here called "SAG12", was isolated along with the genomic clone corresponding to the SAG12 cDNA. The SAG12-1 promoter was isolated from this genomic material. The term "SAG" designates a senescence associated gene.

SEQ ID NO:1 and FIG. 3 contain a nucleotide sequence for one embodiment of the SAG12-1 promoter. SEQ ID NO:2 describes a truncated version of this promoter. Both versions of the SAG12-1 promoter are sufficient to promote gene expression in a senescence-specific manner.

Also described below is a second senescence-specific promoter, isolated from Arabidopsis in a similar manner. The second promoter is here designated "SAG13." The SAG13 promoter was also isolated from the Arabidopsis genome. SEQ ID NO:3 contains the nucleotide sequence for the SAG13 promoter, including 1782 base pairs upstream of the transcription start site.

By "senescence-specific promoter" it is meant to indicate that the SAG12-1 and SAG13 promoters are capable of preferentially promoting gene expression in a plant tissue in a developmentally regulated manner such that expression of a 3' protein coding region occurs substantially only when the plant tissue is undergoing senescence.

Preferably, the SAG12 promoter includes nucleotides sufficiently homologous to the first 602 bp of SEQ ID NO:2 so that the promoter is capable of expressing genes preferably in a senescing tissue. Also, the senescence-specific promoter can consist of the nucleotide sequence of SEQ ID NO:2.

Preferably the SAG13 promoter includes a portion of the sequence set forth in SEQ ID NO:3 below. While this entire sequence is sufficient for senescence-specific promoter activity, it is also likely that a smaller sequence will also be sufficient. The bounds of such a smaller sequence can readily be determined by truncation of the sequence of SEQ ID NO:3 below, followed by empirical testing of such truncations for senescence specific promoter activity.

The Examples below describe the creation of senescence-specific cDNA clones from Arabidopsis, the characterization of these clones, and the use of these cDNA clones to obtain a specific SAG12 senescence-specific promoter, SAG12-1 and a second promoter SAG13. It is believed that there are other senescence-specific promoters with sufficient homology to SAG12-1 or SAG13 to be suitable for the present invention. One could easily use the techniques described below to obtain these homologous promoters.

Creation of an SAG12 Promoter

In the Examples below, described is the isolation of the SAG12 promoter using the SAG12 cDNA clone. This cDNA clone was obtained from an RNA molecule that appears to be expressed only during senescence.

The SAG12 cDNA has been used to screen an Arabidopsis library to obtain the SAG12 gene. The gene was originally designated SAG12-1 in the belief that there were two SAG12 genes in Arabidopsis, although it is now believed that there is only one. The SAG12-1 promoter was obtained from the SAG12-1 genomic clone. SEQ ID NO:1 and FIG. 3 disclose the sequence of 2073 bp of the SAG12-1 promoter. Further studies, also described below, showed that the SAG12-1 promoter could be truncated to 602 bp and still remain functional. SEQ ID NO:2 describes the 602 bp linked to a 5' untranslated region of the SAG12-1 gene.

To obtain a SAG12 promoter, one could follow several paths. Most easily, one could create an oligonucleotide probe from the sequences disclosed in SEQ ID NOs:1 and 2 or FIG. 3 and probe an Arabidopsis genomic library to recover a copy of the SAG12 promoter.

It is envisioned that minor nucleotide additions, deletions, and mutations will not affect the function of the SAG12-1 promoter. Furthermore, it is possible, if not likely, that there may be variations in sequence of the SAG12 gene (or SAG13) and promoter among populations of Arabidopsis stocks because of normal allelic variations. Furthermore, it is likely and anticipated that homologous sequences can be recovered from other plants. Therefore, the sequence of a suitable SAG promoter might not be identical to that disclosed in SEQ ID NOs:1 or 2. Detailed below is an assay by which one may determine whether a candidate genomic sequence is sufficiently homologous to the senescence-specific SAG12-i promoter to be suitable for the present invention.

Additionally, it is envisioned that the 602 bp of SEQ ID NO:1 may be further truncated and still produce a suitable SAG12 promoter. One of ordinary skill in this technology can readily appreciate that 5' or 3' truncations, or internal deletions, from this 602 bp sequence can be made, and those truncations empirically tested for senescence-specific activity, to find such smaller truncations of the SAG12-1 promoter.

Preferably, a portion of the 5' untranslated region of the SAG12-1 gene will be added to the promoter sequence. SEQ ID NOs:1 and 2 disclose this sequence. In FIG. 3, the 5' untranslated region is the region between the +1 symbol and the "Nco I" symbol.

Creation of SAG13 Promoter

A similar method was used to isolate and identify the SAG13 promoter set forth in the Examples below. Variations in SAG13 sequence, due to allelic variations and the like, are expected as well. SAG12 and SAG13 are not notably homologous.

Assay of a Candidate Promoter

Once a candidate genomic sequence has been isolated, one may wish to determine whether or not this DNA sequence is a SAG12 or a SAG13 promoter. One could sequence the DNA sequence by techniques familiar to those skilled in the art of plant molecular biology and determine whether the sequence is identical to either SEQ ID NO:1, 2 or 3. If the candidate sequence is identical or homologous to a portion of the first 2073 bp of SEQ ID NO:1, the first 602 bp of SEQ ID NO:2, or the first 1782 bp of SEQ ID NO:3, then the sequence is a suitable SAG12 or SAG13 promoter.

If the sequence is not identical, however, and is closely homologous, i.e. more than 95% homologous, one i5 may have isolated a copy of an allelic SAG12 or SAG13 promoter. One would wish to do a functional assay to determine whether or not this sequence was sufficiently homologous to the first 602 bp of SEQ ID NO:2, the first 2073 bp of SEQ ID NO: 1, or the first 1782 bp of SEQ ID NO:3 to be suitable for the present invention.

By "sufficiently homologous" it is meant that a candidate promoter is at least 95% homologous in nucleotide sequence and is substantially equivalent to the SAG12-1 promoter sequence in its ability to preferentially promote gene expression in senescing plant tissue. An assay for determining whether a candidate sequence is suitable is described below.

To make this determination, one could follow the examples described below and attach the candidate promoter to a reporter protein coding sequence, such as the GUS sequence encoding the enzyme beta-glucuronidase. The sequence of the GUS gene is described in U.S. Pat. No. 5,268,463. Transformation of a plant with an expression cassette including the GUS sequence allows one to determine whether or not the GUS reporter sequence was expressed in only the senescing tissues, was constitutively expressed, or was not expressed at all. Only a result indicating that the reporter sequence is only expressed in senescing tissues and not other tissues would indicate a suitable promoter.

Alternatively, the candidate sequence could be attached to the isopentenyl transferase sequence and transformed into tobacco plants, as we have described below. Table 2 of the Examples discloses specific differences between plants transformed with the SAG12 promoter linked to an IPT gene and transgenic control plants containing a construct with the SAG12 promoter linked to the GUS reporter gene. A candidate promoter would have to perform equivalently to be suitable for the present invention.

Therefore, a candidate promoter must satisfy three criteria. First, it must be isolatable or hybridizable with an oligonucleotide probe created from the first 2073 bp or SEQ ID NO:1, the first 602 bp of SEQ ID NO:2, or the corresponding portion of SEQ ID NO:3. Second, it must be sufficiently homologous to either the first 2073 bp of SEQ ID NO:1, the first 602 bp of SEQ ID NO:2, or the corresponding portion of SEQ ID NO:3 so as to promote senescence-specific expression of a reporter gene, such as GUS. Third, it must provide equivalent senescence-specific expression as the SAG12 or SAG13 promoter described in Table 2 of the Examples.

Creation of Genetic Construct

Once one has obtained an SAG12 or SAG13 promoter, a genetic construct must be created containing both that promoter and a protein-coding sequence. By "genetic construct" it is meant to describe an operably connected promoter and gene sequence. Typically the promoter sequence is 5' or "upstream" of the gene sequence. The promoter will be able to promote transcriptional activity using the gene sequence as a template.

A suitable foreign gene sequence is capable of expressing an RNA molecule. This RNA molecule may or may not be translated into a mature protein. A "foreign gene sequence" may alternatively be in the antisense orientation in order to express antisense mRNA. Preferably, the foreign gene sequence encodes a protein.

In one embodiment of the invention, the foreign gene sequence encodes an enzyme catalyzing biosynthesis of a plant hormone, preferably a cytokinin. Most preferably, the enzyme is IPT (isopentenyl transferase).

Standard molecular biological procedures may be used to link the cloned promoter to a protein-coding sequence, such as the IPT sequence. Several genes encoding IPT have been isolated, sequenced and published. The bacterial strains harboring these genes have been deposited with, and are available from, ATCC. With published sequence information, PCR and other gene amplification and recovery techniques may be used to isolate IPT genes. Examples of IPT sequences (also referred to as tmr or tzs) are presented in: Crespi et al., *EMBO J.* 11:795–804 (1992); Goldberg et al., *Nucleic Acids. Res.* 12:4665–4677 (1984); Heide Kamp et al., *Nucleic Acids Res.*, 11:6211–6223 (1983); Strabala et al., *Mol. Gen. Genet.* 216:388–394 (1989).

The genetic construct may be created using either plasmid or viral vectors or other methods known in the art of molecular biology to create a construct capable of being transformed into a plant cell. We describe the creation of a genetic construct suitable to be transformed via the Agrobacterium system. However, there are other means of transformation of plants, and creation of transgenic plants, such as particle bombardment and electroporation, that require many different vector systems. The ability to construct and adopt such vectors to the transformation system to be used is well known to those of skill in the art.

Modification of Plant Senescence

The availability of effective plant senescence-specific promoters makes possible the creation of transgenic plants with altered senescence characteristics. Genetic constructs can be inserted into plants which become effective only upon plant cells entering senescence. Such senescence-specific expression permits the expression in plants of genes which might be disruptive of plant morphology or productivity if expressed at any other stage of plant development. For example, it now becomes possible to insert a gene encoding a cytokinin biosynthetic enzyme under the control of a senescence-specific promoter without having the tissues of the plant exposed to the excess cytokinin during pre-senescence growth. Then, at the onset of senescence, the senescence-specific promoter activates cytokinin production to alter the progression of senescence in the plant. It has been found, in particular, that the combination of a senescence-specific promoter and a cytokinin-producing gene sequence creates a transgenic plant that, in essence, has a delayed senescence. Such a plant will vegetatively grow longer, producing more flower, seed or fruit, than a corresponding non-transgenic plant. It is anticipated that other coding regions affecting plant maturation and senescence may also be placed behind the senescence-specific promoter and transformed into plants to produce useful transgenic plants with altered senescence.

EXAMPLES

Materials and Methods

Plant materials

*Arabidopsis thaliana* ecotype Landsberg erecta seed was sterilized in 2.5% sodium hypochlorite for 5 min and rinsed with five changes of sterile water. Sterile seed was imbibed at 4° C. in 1 mM gibberellic acid $A_3$ for 5 hours prior to sowing on a mixture of peat moss, vermiculite and perlite (1:1:1) saturated with Arabidopsis nutrient solution as described in Somerville, et al., *Methods in Chloroplast Molecular Biology*, Elsevier Biomedical Press, New York, N.Y., pp. 129–137, 1982. Plants were grown at 23° C. and 60% relative humidity under 120 μmol $m^{-2}$ $s^{-1}$ of continuous light from a mixture of cool-white fluorescent (80%) and incandescent (20%) bulbs and sub-irrigated as needed with water. Under these conditions the plants grew vegetatively for about 3 weeks forming 6–7 rosette leaves prior to bolting. Rosette leaves 5 and 6 were harvested at various times after full expansion. All tissues were frozen in liquid $N_2$ immediately after harvest and stored at −80° C.

Quantification of chlorophyll and protein

Forty-five $cm^2$ of fresh leaves were soaked at 65° C. for 2 h in ethanol, and the amount of chlorophyll was determined spectrophotometrically (Wintermans, et al., *Biochem. Biophys. Acta.* 109:448–453, 1965). After ethanol incubation the same leaves were used for total protein extraction after they had been briefly dried under vacuum. The leaf residue from forty-five cm² of leaf material was ground in liquid N₂, resuspended in 9 ml of 10 mM Na₂Citrate, 1 mM EDTA, 1% SDS, pH 8 and incubated at 70° C. with stirring for 30 min. The soluble and insoluble components were separated by centrifugation. The pelletable fraction was solubilized in 10 ml 1N NaOH overnight at 30° C. Protein levels in the soluble and pelletable fractions were subsequently quantified according to Lowry, et al., *J. Biol. Chem.* 193:265–275, 1951 combining the modifications of Peterson, *Anal. Biochem.* 83:346–356, 1977 and Larson, et al., *Anal. Biochem.* 155:243–248, 1986. Three replica samples from three independent batches of Arabidopsis were analyzed.

RNA analysis

Total RNA was extracted as described in Puissant, et al., *BioTechniques* 8:148–149, 1990 and quantitated spectrophotometrically (Sambrook, et al., *Molecular Cloning: A Laboratory Manual*, Cold Spring Harbor Press, N.Y., 1989). For RNA gel blot analyses, RNA samples were. electrophoretically fractionated on formaldehyde-agarose gels, transferred to polysulfone membranes (Gelman, Ann Arbor, Mich.), and hybridized to $^{32}$P-labelled probes made by the random prime method (John, et al., *J. Bacteriol.* 170:790–795, 1988). RNA was loaded on a mass basis (5 µg of RNA per lane) and an area basis (a half leaf equivalent of RNA per lane). The amount of probe hybridized to the RNA was quantitated using a Betagen β-particle scanner (Intelligenetics, Inc., Mountain View, Calif.). RNA gel blots prepared from three independent batches of tissue were analyzed for each cDNA clone.

Construction and screening of cDNA libraries

Poly (A)+ RNA used for construction of cDNA libraries was isolated as described in Crowell, et al., *Proc. Natl. Acad. Sci. USA* 87:8815–8819, 1990. RNA isolated from S2 and pooled S3 and S4 leaves was used to construct two cDNA libraries. First-strand cDNA was synthesized using oligo (dT)$_{17}$-Xba I as primer with SuperScript™ RNase H⁻ reverse transcriptase and second-strand cDNA was synthesized using *E. coli* DNA Polymerase I, *E. coli* DNA ligase and RNAse H as recommended by the manufacturer (BRL, Gaithersberg, Md.). Double-stranded cDNA was size-fractionated on a BioGel A 0.5 m column (BioRad, Richmond, Calif.) to remove cDNAs less than 200 bp in length. EcoR I linker-adapters (Promega, Madison, Wis.) were ligated onto the cDNA then the 5' ends of the cDNA were then phosphorylated with polynucleotide kinase. The cDNA was size fractionated by agarose-gel electrophoresis and cDNAs >500 bp were electroeluted and ligated into pBluescript SKII(+) (Stratagene, La Jolla, Calif.) that had been cut with EcoR I and dephosphorylated. The ligation products were electroporated into *E. coli* strain DH5α. Both S2 and S3/4 cDNA libraries contained 1×10⁵ recombinant clones. For library screening, replica filters of the libraries were prepared as described (Sambrook, et al., 1989, supra) and hybridized to cDNA probes made by reverse transcription of poly (A)+ RNA using deoxyadenosine 5-[α-$^{32}$P] triphosphate. For cross-hybridization analysis, probes corresponding to cDNA inserts were prepared using the random prime method and hybridized to dot blots of candidate plasmids (Sambrook, et al. 1989, supra).

Leaf Senescence in *Arabidopsis thaliana* Proceeds through Defined Phenotypic and Biochemical Changes We divided *Arabidopsis thaliana* rosette leaf senescence into five stages designated S1 through S5 based on phenotypic appearance and measured the amount of RNA, protein, and chlorophyll present at each stage. Leaves at the S1 stage of senescence show the first visible sign of senescence—loss of chlorophyll at the tip of the leaf. As a leaf progresses through senescence, additional loss of chlorophyll occurs. In stage S2, S3, S4, and S5 leaves approximately 25%, 25–50%, 50–75%, and greater than 75% of the leaf area has become yellow. Our visual assessment of these stages corresponds to specific levels of chlorophyll loss. Under our growth conditions, leaves reach stage S1, S2, S3, S4, and S5 at 3, 5, 7, 9, and 10 days after full leaf expansion, respectively.

During senescence, the amount of RNA, protein, and chlorophyll present in a leaf declines. This decrease of RNA and protein has begun by the time chlorophyll loss is first noticeable (stage S1), and continues as the leaf progresses through the senescence program. There is a highly reproducible correlation between the amount of chlorophyll loss and the decline in protein and RNA levels.

Isolation of Senescence-Associated Genes

To identify mRNAs that increase in abundance in Arabidopsis leaves during senescence, we differentially screened a cDNA library constructed from mRNA from senescing leaves. Specifically, two cDNA libraries were constructed from template RNA isolated from S2 leaves and a mixture of S3 and S4 leaves. The S2 and S3/4 cDNA libraries were differentially screened with cDNA probes made by reverse transcribing poly (A)+ RNA isolated from non-senescent (NS) leaves and poly (A)+ RNA isolated from S2 or S3/4 leaves, respectively.

Differential screening of the S3/4 cDNA library identified mRNAs that increase in abundance during senescence. From this library, 23 cDNA clones that hybridized more strongly to the S3/4 cDNA probe than the NS cDNA probe were selected for further characterization. We refer to this class as senescence-associated genes (SAGs). Cross-hybridization analyses indicated that this collection comprised six cDNA species. The longest cDNA of each family was used in subsequent analyses. The sizes of the mRNAs that correspond to the SAG cDNAs are presented below in Table 1.

TABLE 1

| Approximate mRNA sizes in nucleotides of SAGs | |
|---|---|
| SAG | Size |
| 12 | 1360 |
| 13 | 1340 |
| 14 | 1140 |
| 15 | 4560 |
| 16 | 1150 |
| 17 | 800 |

Differential screening of the S2 cDNA library with NS and S2 cDNA probes revealed that the vast majority of the differentially expressed clones hybridized more strongly to the NS cDNA probe than to the S2 cDNA probe. Such cDNA clones correspond to mRNAs that decrease in abundance during senescence. During senescence the photosynthetic output of a leaf and the levels of transcripts encoding proteins required for photosynthesis declines (Hensel, et al., 1993, supra). Therefore, cDNAs corresponding to transcripts encoding photosynthesis-associated proteins are likely to be in this group of clones that decrease in abundance during senescence. Six cDNAs that hybridized more strongly to the NS than the S2 cDNA probe were arbitrarily chosen for further study to provide a contrast to the SAG cDNAs. We designated these clones senescence-down-regulated genes (SDGs) 1 through 6. We wish to emphasize that the SDGs 1–6 correspond to only a small fraction of the cDNAs in the library showing a sharp decline in abundance during senescence.

Gene Expression During Natural Leaf Senescence

The steady-state mRNA levels corresponding to the isolated cDNA clones were investigated temporally throughout leaf senescence. This collection of cDNAs was isolated on the basis of differential expression on a mass basis. Specifically, replica filters of the libraries were screened with an equal mass (measured by dpm) of s2P-labeled cDNA made by reverse transcription of poly (A)+ RNA isolated from NS or senescing leaves. Since the amount of total RNA present in a leaf decreases during senescence, it is possible that the levels of poly (A)+ mRNA decline correspondingly. If the levels of poly (A)+ mRNA decline during senescence, the differential cDNA screening may have revealed SAG clones corresponding to messages that remain constant during senescence when expression is examined on a per cell basis but increase in abundance when expression is examined as a function of RNA mass. For example, an SAG message that remains at a constant level on a per cell basis would appear to increase in abundance on a mass basis if the levels of the majority of mRNAs were declining.

To address whether SAG mRNA levels increase during senescence, we examined the expression of these messages as a function of both mass and leaf area at each stage of senescence. The steady-state RNA levels corresponding to the SAG genes increase during senescence when examined on both a mass and area basis. The increase based upon leaf area demonstrates that SAG mRNA levels per cell are increasing during senescence. When examined on a mass basis, the levels of all SAG mRNAs are maximal at the later stages of senescence (S3-S5). However, when measured on a leaf area basis, certain SAG mRNAs (e.g., 13 and 15) reproducibly exhibit maximal levels at earlier stages of senescence. SAG12 exhibits one of the highest levels of induction and, within the limits of detection methods, appears to be expressed only during senescence. There is no detectable SAG12 signal in lanes of RNA from non-senescent leaves even with long exposures of the autoradiograph or when measured by a β particle collector. The levels of SAG12 mRNA increase throughout the progression of senescence and reach maximal levels at the last stage of senescence examined.

The steady-state RNA levels corresponding to the six downregulated genes decrease during senescence when examined as a function of both RNA mass and leaf area. As expected, the reduction is much greater when the expression is examined as a function of area than of mass. As discussed above, the majority of mRNAs in the leaf appear to follow this pattern, including mRNAs corresponding to nuclear-encoded genes involved in photosynthesis such as the chlorophyll a/b binding protein (CAB) and the small subunit of ribulose bisphosphate carboxylase/oxygenase (Rubisco) (Hensel, et al., 1993, supra). We also examined CAB mRNA levels during the stages of senescence that we have defined. We found that CAB mRNA levels drop during leaf senescence at approximately the same rate as the SDGs. However, cross-hybridization analyses indicated that none of the 6 SDG clones were members of the CAB or Rubisco gene families.

Isolation of a Senescence-Specific Promoter

We screened an Arabidopsis genomic library with the SAG12 cDNA for clones that contained the SAG12 promoter region of the SAG12. The library was provided by David Marks of the University of Minnesota.

Figure 2:
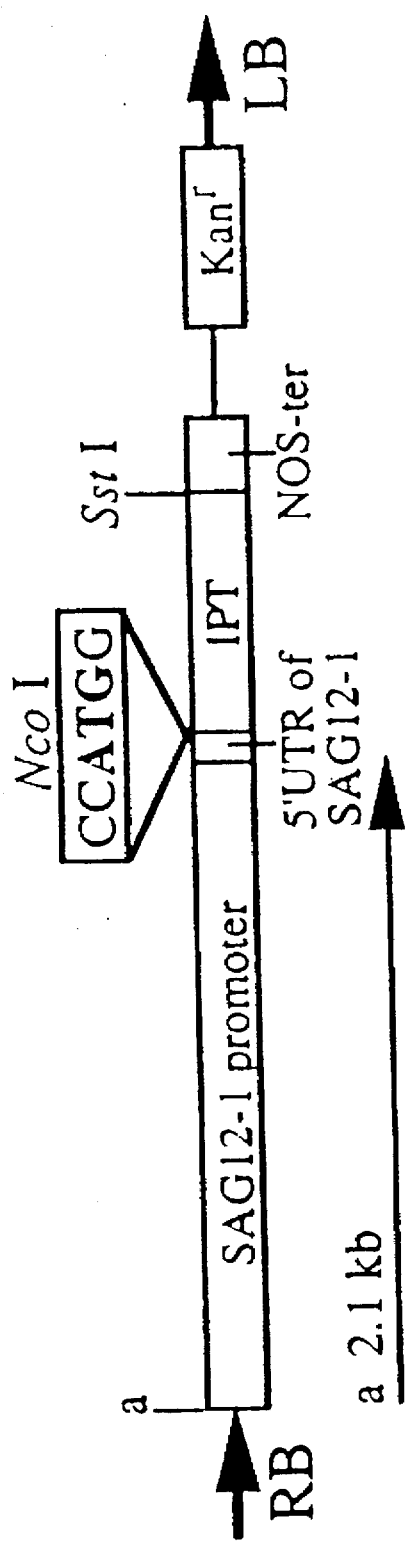
FIG. 2 is a schematic map of SAG12-1 promoter/IPT/NOS-ter construct in a binary vector.

We found that there is one copy of SAG12 in the Arabidopsis genome. FIG. 1 is a diagram of a construct containing 2073 bp of the SAG12-1 promoter and the 5' untranslated region attached to the GUS reporter gene. FIG. 2 is a diagram of the nucleotide sequence of the SAG12-1 promoter linked to the SAG12-15' untranslated sequence, the isopentenyl transferase gene and the NOS termination sequence.

The SAG12-1 promoter fragment (from the EcoR V site at −2073 through an Nco I site artificially created at the SAG12-1 start codon by oligo mutagenesis) was cloned into pGEM5Zf(+) (Promega, Madison, Wis.) EcoR V-Nco I sites. This construct was named pSG499. A 2.6 kb Sal I-Sal I fragment containing 1.87 kb GUS and 0.8 kb MAS terminator was cloned into pUC18 Sal I site. The MAS terminator is described in Plant Mol. Biol. 15:373–381 (1990). This construct was named pSG468-2. The 2.2 kb SAG12-1 promoter from the Nco I site to the Pst I site in pSG499 was cloned into pSG468-2 at the Nco I-Pst I sites. This construct was named pSG506. The Pst I-Xba I fragment containing SAG12-1 promoter:GUS:MAS-ter was subsequently cloned into a binary vector at the Pst I-Xba I sites, resulting in the construct shown in FIG. 1.

A 1 kb Nco I-Xba I fragment containing 0.7 kb IPT and 0.3 kb NOS terminator sequences (Yi Li, et al., Dev. Biol. 153:386–395, 1992) was cloned into pSG506 at the Nco I-Xba I sites to replace GUS:MAS-ter fragment. This new construct was named pSG516. The Spe I-Spe I fragment containing SAG12-1 promoter:IPT:NOS-ter in pSG516 was then cloned into a binary vector at the Xba I site (both Spe I and Xba I have compatible cohesive restriction ends), resulting in the construct shown in FIG. 2.

We mapped the start site of transcription of SAG12-1 (indicated as +1 in FIG. 3) and fused a 2180 bp fragment containing 2073 bp upstream of this start site and the 107 bp SAG12-15' untranslated region (UTR) to two genes: the reporter gene beta-glucuronidase (GUS) and isopentenyl transferase (IPT), an enzyme catalyzing the rate-limiting step of cytokinin biosynthesis. The promoter fragment begins at point "a" in FIGS. 1, 2 and 3. SEQ ID NO:1 is the sequence of the SAG12-1 promoter, the IPT gene and the NOS-ter sequence.

These genes were introduced into the genome of both Arabidopsis thaliana (Arabidopsis) and Nicotiana tabacum (tobacco) by Agrobacterium-mediated transformation (Horsch, et al., Science 227:1229–1231, 1985; Valvekens, et al., Proc. Natl. Acad. Sci. USA 87:5536–5540, 1988). The resulting plants were fixed and assayed for expression of the GUS gene by colorimetric assay. Analysis of transgene expression demonstrated that the SAG12-1 genomic sequence fused to the reporter gene contains a senescence-specific promoter. In both Arabidopsis and tobacco, the GUS reporter gene was expressed in senescing leaves but was not detectable in leaves prior to senescence.

In transgenic tobacco we have done more extensive analyses and found that the SAG12-1 promoter is also active in flower parts during senescence. This result is not surprising since floral organs are developmentally and evolutionarily related to leaves (i.e., floral organs are thought of as modified leaves).

We found that a 709 bp fragment (602 bp upstream of the start of transcription; point "b" in FIG. 1) fused to the GUS gene results in a pattern of GUS expression in transgenic plants which is identical to that observed with the 2180 bp fragment. Thus, this smaller region contains all of the regulatory signals required for senescence-specific regulation. SEQ ID NO:2 is the 602 bp upstream from the start of transcription in the SAG12-1 gene and 107 bp of the 5' untranslated region.

Use of the Senescence-Specific Promoter to Delay Senescence

Cytokinins have been shown to be effective at blocking leaf senescence in both detached leaves and leaves undergoing natural senescence on the plant in many species including both monocots and dicots (for review see Noodén, Senescence and Aging in Plants, pp. 391–439, 1988 and Van Staden, et al., Senescence and Aging in Plants, pp. 281–328, 1988). Moreover, the prevention of senescence by cytokinins results in the maintenance of a photosynthetically active leaf. Several studies have demonstrated that cytokinin treatment stimulates photosynthesis and chloroplast and cytoplasmic protein synthesis while preventing chloroplast breakdown (Van Staden, et al., supra).

While most studies on the effects of cytokinins on senescence have involved application of exogenous cytokinins, there is evidence that endogenously produced cytokinins are a natural regulator of leaf senescence. Noodén, et al. (Noodén, et al., *Plant Physiol.* 93:33–39, 1990) have recently studied cytokinin fluxes in soybean leaves that are undergoing natural senescence on the intact plant. During the later stages of seed development that trigger senescence in soybean, the flux of cytokinins from roots to leaves is drastically reduced. Moreover, removal of seed pods reverses senescence and restores the flux of cytokinins to leaves. Further support is provided by transgenic plant studies. The isopentenyl transferase gene (IPT) from the T-DNA of the *Agrobacterium tumefaciens* Ti plasmid catalyzes the rate-limiting step in the biosynthesis of cytokinins. Transgenic plants that overexpress the IPT gene often exhibit some delay of leaf senescence (Li, et al., *Dev. Biol.* 153:386–395, 1992; Ooms, et al., *Plant Mol. Biol.* 17:727–743, 1991; Smart, et al., *The Plant Cell* 3:647–656, 1991). However, IPT expression in these transgenic plants was not leaf specific and therefore the transgenic plants displayed developmental abnormalities typical of general cytokinin overproduction such as stunted root growth and lack of apical dominance.

The goal was to target cytokinin production to senescing leaves at a level that will block senescence but does not interfere with other aspects of plant development.

Eight transgenic tobacco lines were created using the genetic construct illustrated in FIG. 2. All eight transgenic tobacco lines that expressed the SAG12-1/IPT fusion were perfectly normal phenotypically (i.e., there were no alterations of branching, flower development, root growth, etc.) except that all of the leaves of the transgenic plants retained high levels of chlorophyll throughout flower and seed development. Nontransformed control plants and plants transformed with a construct similar to the SAG12-1/IPT fusion, except that IPT sequences were replaced with the GUS gene, exhibited extensive senescence of lower leaves during flower and seed development. Thus, the goal of altering senescence was achieved without perturbing other aspects of plant development.

The transgenic plants had greatly enhanced yield of biomass and flower and seed production. As shown in Table 2 below, total biomass and flower number were greatly increased in the IPT transgenic plants as compared to transgenic controls that express GUS, although leaf number and flowering time were the same. The seed yield per flower was the same in control and IPT plants; therefore, the seed yield was almost doubled in the IPT transgenic plants. The IPT transgenics were still growing (the controls had stopped growing) when the experiment was terminated due to insect infestation and the actual increase in yield would probably have been greater if the experiment could have been continued. Thus, this system is of potential use to increase yield of both biomass and seed and enhance flower production in ornamental crops.

We have also put the SAG12-IPT construct shown in FIG. 2 into Arabidopsis and shown that it blocks leaf senescence in this species as well.

The SAG12-1/IPT construct was made with an IPT construct provided by Yi Li (Li, et al., *Dev. Biol.* 153:386–395, 1992). The useful feature of this IPT gene was the introduction of an Nco I site at the start of translation. The IPT gene was readily available from our previous work (See, for example, Akiyoshi, et al., *Proc. Natl. Acad. Sci. USA* 81:5994–5998), but we chose Li's construct to save a cloning step. This construct utilizes a "terminator" (a sequence that makes a proper 3' end on the mRNA) from the nopaline synthase gene (NOS) (Bevan, et al., *Nucleic Acids Research* 11:369–385, 1983).

Isolation of SAG13 Promoter

In the mRNA library described above, 23 cDNA clones were identified associated with leaf senescence. The identification of one, SAG12 is described above, and similar methods were used to identify SAG13 and its associated promoter.

The SAG13 clone contained a 1.24-Kb insert. This insert was used to make a probe to screen the Arabidopsis genomic library described above. Two unique genomic clones were found. (i.e., there are two copies of SAG13 in the Arabidopsis genome.) The two clones contained a 3.53 kb EcoRI-SalI fragment that contains the region upstream of the start site of transcription. These DNA fragments were subcloned into pBluescript II SK vector at the EcoRI and SalI sites and were subsequently sequenced. The fragment contained all the SAG13 cDNA sequence and an upstream promoter sequence. The sequence of the SAG13 upstream promoter sequence is set forth in SEQ ID NO:13 below. The transcription start site is at nucleotide 1782 and the translation start site is at nucleotide 1957. The two sequences were identical except at position 1009 where one copy of the gene contains a G residue and the other copy an A residue.

TABLE 2

Comparison of some characteristics of SAG12-ipt transgenic and related plants

| | Wisconsin 38 (Wild-type) | SAG12-gus Plants | SAG12-gus/ SAG12-ipt Plants | SAG12-ipt Plants |
|---|---|---|---|---|
| Chlorophyll content ($\mu$g $cm^{-2}$ leaf #7) | | | | |
| 39-day-old[a] | 19.911 ± 0.642 | 21.627 ± 1.893 | 22.117 ± 1.944 | 25.638 ± 1.877 |
| 68-day-old[b] | 1.239 ± 0.719 | 1.797 ± 1.575 | 16.905 ± 1.551 | 18.527 ± 2.855 |
| Protein content ($\mu$g $cm^{-2}$ leaf #7) | | | | |
| 39-day-old[a] | 52.47 ± 1.75 | 52.27 ± 1.01 | 71.33 ± 7.04 | 71.60 ± 3.86 |
| 68-day-old[b] | 16.00 ± 5.29 | 19.60 ± 10.65 | 54.40 ± 3.49 | 49.60 ± 5.88 |
| Total flower # | 178.3 ± 28.1 | 176.2 ± 51.1 | 318.6 ± 44.2 | 327.5 ± 46.3 |
| Seed yield (g/plant) | 20.436 ± 4.182 | 21.142 ± 3.683 | 30.240 ± 4.037 | 31.154 ± 4.100 |
| Biomass (g/plant)[c] | 107.51 ± 14.41 | 101.64 ± 10.97 | 151.80 ± 20.40 | 150.79 ± 20.15 |
| Plant height (cm)[d] | 176.25 ± 14.27 | 172.54 ± 6.70 | 178.38 ± 10.54 | 180.15 ± 7.91 |
| Leaf # on main stem | 33.3 ± 0.5 | 33.0 ± 0.9 | 33.1 ± 1.0 | 33.5 ± 1.4 |

[a]The #7 leaves of all genotype plants were fully expanded but nonsenescent after 39 days of their emergence.
[b]The #7 leaves of both wild-type and SAG12-gus plants were completely senesced after 68 days of emergence.
[c]Dry weight of the above soil of the plant excluding seeds.
[d]From the soil surface to the toppest floral stalk.
Sample Sizes: Wisconsin 38: 8 plants; SAG12-gus: 13 plants; SAG12-gus/SAG12-ipt: 8 plants; SAG12-ipt: 13 plants.

We claim:

1. A genetic construct comprising an Arabidopsis-derived SAG12 or SAG13 promoter sequence operably connected to a protein-coding DNA sequence not natively connected to the promoter sequence.

2. The construct of claim 1 wherein the promoter sequence comprises the first 602 bp of SEQ ID NO:2.

3. The construct of claim 1 wherein the promoter sequence comprises the first 1782 bp of SEQ ID NO:3.

4. The construct of claim 1 wherein the protein-coding sequence encodes a plant hormone synthesizing enzyme.

5. The construct of claim 4 wherein the protein-encoding sequence encodes an enzyme catalyzing the synthesis of the plant hormone cytokinin.

6. The construct of claim 5 wherein the protein-encoding sequence encodes isopentenyl transferase.

7. The construct of claim 1 additionally comprising the SAG12-1 5' untranslated region.

8. A genetic construct comprising an Arabidopsis-derived SAG12 promoter operably connected to a DNA sequence encoding an enzyme catalyzing the synthesis of cytokinin.

9. The construct of claim 8 wherein the DNA sequence codes for isopentenyl transferase.

10. A cell containing the construct of claim 2.

11. A cell containing the construct of claim 8.

12. A plant containing the construct of claim 1.

13. A plant containing the construct of claim 8.

14. A genetic construct comprising an Arabidopsis-derived SAG13 promoter operably linked to a DNA sequence encoding an enzyme catalyzing the synthesis of cytokinin.

15. A transgenic plant with delayed senescence, the plant comprising in its genome, 5' to 3', a genetic construction comprising a senescence associated promoter and a coding region for an enzyme catalyzing the synthesis of a cytokinin, wherein the promoter is Arabidopsis-derived SAG13.

16. A transgenic plant having delayed senescence characteristics comprising in its genome a foreign genetic construction which comprises 5' to 3', a senescence specific promoter, a protein coding region for an enzyme which when expressed will catalyze the production of a cytokinin in the cells of the plant, and a transcriptional termination sequence, wherein the foreign genetic construction is expressed in tissues entering senescence to delay the senescence of the plant tissues and wherein the promoter is Arabidopsis-derived SAG 12-1.

17. A transgenic plant having delayed senescence characteristics comprising in its genome a foreign genetic construction which comprises 5' to 3', a senescence specific promoter, a protein coding region for an enzyme which when expressed will catalyze the production of a cytokinin in the cells of the plant, and a transcriptional termination sequence, wherein the foreign genetic construction is expressed in tissues entering senescence to delay the senescence of the plant tissues and wherein the promoter is Arabidopsis-derived SAG13.

18. Seed of the plant of claim 12.
19. Seed of the plant of claim 13.
20. A plant containing the construct of claim 14.
21. Seed of the plant of claim 20.
22. Seed of the plant of claim 15.
23. Seed of the plant of claim 16.
24. Seed of the plant of claim 17.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 3183 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="SAG12-1 Promoter DNA"

( x i ) SEQUENCE DESCRIPTION: SEQ ID NO:1:

```
GATATCTCTT TTTATATTCA AACAATAAGT TGAGATATGT TTGAGAAGAG GACAACTATT      60
CTCGTGGAGC ACCGAGTCTG TTTTATATTA GAAACCCGAT TGTTATTTTT AGACTGAGAC     120
AAAAAAGTAA AATCGTTGAT TGTTAAAATT TAAAATTAGT TTCATCACGT TTCGATAAAA     180
AAATGATTAG TTATCATAGC TAATATAGCA TGATTCTAAA TTTGTTTTTT GACACCCTTT     240
TTTTCTCTCT TTGGTGTTTT CTTAACATTA GAAGAACCCA TAACAATGTA CGTTCAAATT     300
AATTAAAAAC AATATTTCCA AGTTTATAT ACGAAACTTG TTTTTTTAAT GAAAACAGTT      360
GAATAGTTGA TTATGAATTA GTTAGATCAA TACTCAATAT ATGATCAATG ATGTATATAT     420
ATGAACTCAG TTGTTATACA AGAAATGAAA ATGCTATTTA ATACCGATC ATGAAGTGTT      480
AAAAAGTGTC AGAATATGAC ATGAAGCGTT TTGTCCTACC GGGTATCGAG TTATAGGTTT     540
GGATCTCTCA AGAATATTTT GGGCCATATT AGTTATATTT GGGCTTAAGC GTTTTGCAAA     600
GAGACGAGGA AGAAAGATTG GGTCAAGTTA ACAAAACAGA GACACTCGTA TTAGTTGGTA     660
CTTTGGTAGC AAGTCGATTT ATTTGCCAGT AAAAACTTGG TACACAACTG ACAACTCGTA     720
TCGTTATTAG TTTGTACTTG GTACCTTTGG TTAAGAAAAA GTTGATATAG TTAAATCAGT     780
TGTGTTCATG AGGTGATTGT GATTTAATTT GTTGACTAGG GCGATTCCTT CACATCACAA     840
TAACAAAGTT TTATAGATTT TTTTTTATAA CATTTTTGCC ACGCTTCGTA AAGTTTGGTA     900
TTTACACCGC ATTTTTCCCT GTACAAGAAT TCATATATTA TTTATTTATA TACTCCAGTT     960
GACAATTATA AGTTTATAAC GTTTTTACAA TTATTTAAAT ACCATGTGAA GATCCAAGAA    1020
TATGTCTTAC TTCTTCTTTG TGTAAGAAAA CTAACTATAT CACTATAATA AAATAATTCT    1080
AATCATTATA TTTGTAAATA TGCAGTTATT TGTCAATTTT GAATTAGTA TTTTAGACGG     1140
TTATCACTTC AGCCAAATAT GATTGGATT TAAGTCCAAA ATGCAATTTC GTACGTATCC     1200
CTCTTGTCGT CTAATGATTA TTTCAATATT TCTTATATTA TCCCTAACTA CAGAGCTACA    1260
TTTATATTGT ATTCTAATGA CAGGGAAACT TCATAGAGA TTCAGATAGA TGAAATTGGT     1320
GGGAAACATC ATTGAACAGG AAACTTTTAG CAAATCATAT CGATTTATCT ACAAAAGAAT    1380
ACTTAGCGTA ATGAAGTTCA CTTGTTGTGA ATGACTATGA TTTGATCAAA TTAGTTAATT    1440
TTGTCGAATC ATTTTTCTTT TTGATTTGAT TAAGCTTTTA ACTTGCACGA ATGGTTCTCT    1500
TGTGAATAAA CAGAATCTTT GAATTCAAAC TATTTGATTA GTGAAAAGAC AAAAGAAGAT    1560
TCCTTGTTTT TATGTGATTA GTGATTTGA TGCATGAAAG GTACCTACGT ACTACAAGAA     1620
AAATAAACAT GTACGTAACT ACGTATCAGC ATGTAAAAGT ATTTTTTCC AAATAATTTA     1680
TACTCATGAT AGATTTTTTT TTTTGAAAT GTCAATTAAA AATGCTTTCT TAAATATTAA     1740
TTTTAATTAA TTAAATAAGG AAATATATTT ATGCAAAACA TCATCAACAC ATATCCAACT    1800
```

-continued

| | | | | | |
|---|---|---|---|---|---|
| TCGAAAATCT | CTATAGTACA | CAAGTAGAGA | AAATAAATTT | TACTAGATAC | AAACTTCCTA | 1860 |
| ATCATCAATT | ATAAATGTTT | ACAAAACTAA | TTAAACCCAC | CACTAAAATT | AACTAAAAAT | 1920 |
| CCGAGCAAAG | TGAGTGAACA | AGACTTGATT | TCAGGTTGAT | GTAGGACTAA | AATGGCTACG | 1980 |
| TATCAAACAT | CAACGATCAT | TTAGTTATGT | ATGAATGAAT | GTAGTCATTA | CTTGTAAAAC | 2040 |
| AAAAATGCTT | TGATTTGGAT | CAATCACTTC | ATGTGAACAT | TAGCAATTAC | ATCAACCTTA | 2100 |
| TTTTCACTAT | AAAACCCCAT | CTCAGTACCC | TTCTGAAGTA | ATCAAATTAA | GAGCAAAAGT | 2160 |
| CATTTAACTT | TCCTAAAACC | ATGGACCCTG | CATCTAATTT | TCGGTCCAAC | TTGCACAGGA | 2220 |
| AAGACGACGA | CCGCGATAGC | TCTTGCCCAG | CAGACAGGGC | TTCCAGTCCT | TTCGCTTGAT | 2280 |
| CGGGTCCAAT | CGTGTCCTCA | ACTATCAACC | GGAAGCGGAC | GACCAACAGT | GGAAGAACTG | 2340 |
| AAAGGAACGA | CGCGTCTCTA | CCTTGATGAT | CGGCCTCTGG | TGGAGGGTAT | CATCGCAGCC | 2400 |
| AAGCAAGCTC | ATCATAGGCT | GATCGAGGAG | GTGTATAATC | ATGAGGCCAA | CGGCGGGCTT | 2460 |
| ATTCTTGAGG | GAGGATCCAC | CTCGTTGCTC | AACTGCATGG | CGCGAAACAG | CTATTGGAGT | 2520 |
| GCAGATTTTC | GTTGGCATAT | TATTCGCCAC | AAGTTACCCG | ACCAAGAGAC | CTTCATGAAA | 2580 |
| GCGGCCAAGG | CCAGAGTTAA | GCAGATGTTG | CACCCCGCTG | CAGGCCATTC | TATTATTCAA | 2640 |
| GAGTTGGTTT | ATCTTTGGAA | TGAACCTCGG | CTGAGGCCCA | TTCTGAAAGA | GATCGATGGA | 2700 |
| TATCGATATG | CCATGTTGTT | TGCTAGCCAG | AACCAGATCA | CGGCAGATAT | GCTATTGCAG | 2760 |
| CTTGACGCAA | ATATGGAAGG | TAAGTTGATT | AATGGGATCG | CTCAGGAGTA | TTTCATCCAT | 2820 |
| GCGCGCCAAC | AGGAACAGAA | ATTCCCCCAA | GTTAACGCAG | CCGCTTTCGA | CGGATTCGAA | 2880 |
| GGTCATCCGT | TCGGAATGTA | TTAGGTTACG | CCAGCCCTGA | GCTCGATCGT | TCAAACATTT | 2940 |
| GGCAATAAAG | TTTCTTAAGA | TTGAATCCTG | TTGCCGGTCT | TGCGATGATT | ATCATATAAT | 3000 |
| TTCTGTTGAA | TTACGTTAAG | CATGTAATAA | TTAACATGTA | ATGCATGACG | TTATTTATGA | 3060 |
| GATGGGTTTT | TATGATTAGA | GTCCCGCAAT | TATACATTTA | ATACGCGATA | GAAAACAAAA | 3120 |
| TATGGCGCGC | AAACTGGGAT | AAATTATCGC | GCGCGGTGTC | ATCTATGTTA | CTAGATCGAA | 3180 |
| TTC | | | | | | 3183 |

( 2 ) INFORMATION FOR SEQ ID NO:2:

( i ) SEQUENCE CHARACTERISTICS:
    ( A ) LENGTH: 709 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="SAG12-1 Promoter DNA
      ( t r u n c a t e d )"

( x i ) SEQUENCE DESCRIPTION: SEQ ID NO:2:

| | | | | | |
|---|---|---|---|---|---|
| AAGCTTTTAA | CTTGCACGAA | TGGTTCTCTT | GTGAATAAAC | AGAATCTTTG | AATTCAAACT | 60 |
| ATTTGATTAG | TGAAAAGACA | AAAGAAGATT | CCTTGTTTTT | ATGTGATTAG | TGATTTTGAT | 120 |
| GCATGAAAGG | TACCTACGTA | CTACAAGAAA | AATAAACATG | TACGTAACTA | CGTATCAGCA | 180 |
| TGTAAAAGTA | TTTTTTTCCA | ATAATTTAT | ACTCATGATA | GATTTTTTT | TTTGAAATG | 240 |
| TCAATTAAAA | ATGCTTTCTT | AAATATTAAT | TTAATTAAT | TAAATAAGGA | AATATATTTA | 300 |
| TGCAAAACAT | CATCAACACA | TATCCAACTT | CGAAAATCTC | TATAGTACAC | AAGTAGAGAA | 360 |
| AATAAATTTT | ACTAGATACA | AACTTCCTAA | TCATCAATTA | TAAATGTTTA | CAAAACTAAT | 420 |
| TAAACCCACC | ACTAAAATTA | ACTAAAAATC | CGAGCAAAGT | GAGTGAACAA | GACTTGATTT | 480 |

| | | | | |
|---|---|---|---|---|
| CAGGTTGATG | TAGGACTAAA | ATGGCTACGT | ATCAAACATC | AACGATCATT TAGTTATGTA | 540 |
| TGAATGAATG | TAGTCATTAC | TTGTAAAACA | AAAATGCTTT | GATTGGATC AATCACTTCA | 600 |
| TGTGAACATT | AGCAATTACA | TCAACCTTAT | TTTCACTATA | AAACCCCATC TCAGTACCCT | 660 |
| TCTGAAGTAA | TCAAATTAAG | AGCAAAAGTC | ATTAACTTT | CCTAAAACC | 709 |

( 2 ) INFORMATION FOR SEQ ID NO:3:

( i ) SEQUENCE CHARACTERISTICS:
        ( A ) LENGTH: 1974 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="SAG13 Promoter DNA"

( x i ) SEQUENCE DESCRIPTION: SEQ ID NO:3:

| | | | | |
|---|---|---|---|---|
| GAATTCTCAG | TGTTCTCTTA | AATCAAATCT | CTCACACTAT | GAGTATATGA ACAAAATCAT | 60 |
| ATACATATCA | CAATTCCATT | ATGGATATCT | CCCAATCTAT | CTCTCATACA TGAAAATGTT | 120 |
| CTATTTCGAT | CTTGTATTTA | ATAATGTTAA | TACTCTGTTT | TAATTGTGT ATCCTGATTT | 180 |
| TTTTTTCTTT | TTGAAGTTCA | ACAAATATAT | CAAAATAACT | CAGAACCATT ACTATTTTT | 240 |
| CTTAGTTCAT | CAATTCTTTA | CTACACATAG | AAACGTATTT | ATCTTGTTTG ATCTACTTTG | 300 |
| ACTCTATATA | TGTCATGTGG | CATCTCTGGT | CATTGCTAGT | CACAGGTAAA AGTAAAATT | 360 |
| GATCAAAGAT | AAAGAGTCTT | TCATGGTAAA | AATTCTCTTG | TAACTGGTGG AGATAGTAGA | 420 |
| TGTCAATTCG | TTTGCAATAA | CTTACATTTG | CAATAACATG | TCAGCCATAT TTATTTAAAT | 480 |
| TTCCATGCAT | TTGATATTAT | TTTCTCTCTA | ATACATATAT | GATGTGTTAC GGTCATTCTA | 540 |
| AAAATCCAGT | TGACAGCATA | ATGAAGCTGG | TACACCATAC | ATGCACTTGA TTATATATGG | 600 |
| ATGTTACTGC | CATGATTGAT | GTTTTGATGG | AATTAGTGTT | AAAGGATGGA CCCTCACTAA | 660 |
| CGCGGTTGGA | AATTATGATC | AAACTCTTCA | ATGTCACTTA | TCAAGAGAGC TAATGACTAG | 720 |
| CACGTTTAGT | TGTTCTGTTG | TTTCTTATGG | CTGCTTAATG | TCTCCATCAA ATATTTAGAC | 780 |
| ATTGTGGCTA | GTAAAATGCC | ATCTACCTTA | ATCCTATATA | TAAGTATAAC TAGATAATAA | 840 |
| TCCATATTTT | TGCTGGGTTT | AGTAGCTGAT | ACGACGTTTA | TGGTTGTTAT TGAGTTTGAA | 900 |
| TACAAAATAT | AGAGTATTGT | TGGAGTTATA | TTGATTTTTG | TTCATATTAG TTAACAAATA | 960 |
| ATAAAAAAAT | TAAGAAAGGT | TTTTGAAAAT | GCATCTTCTA | GAATATATRT ATATTCGAAA | 1020 |
| AAGTCACATC | TTTAATTGAC | ATATGTTTTG | TTTGTTTGTT | TTTTTTACT GGCCACACAA | 1080 |
| ATTGACAACA | ATGGTCATGC | ATGAAATGAA | ATGTTTGTTG | TCAATTTTTT TTACTAACTT | 1140 |
| GTAATATCAT | TATGAAATGA | AATAGAAGGT | ATATATTACA | AAATATTACC TAAAAGTAGA | 1200 |
| GCAATCTTAG | AAAAAAAAAA | AAAAAAAAAA | AAAAAGAAA | AAGAAAAAGA AACAAGATTA | 1260 |
| CAATGCATTT | AAAAAGAGAT | GGAAAGAATC | CGAGCTATCG | AATCCAAAGA AGCATCTACT | 1320 |
| TCCTCCATCT | GTTCTTGTAT | CGTCTACCAG | AGATGGTGTT | CCGGATCTCT CGATCAATAT | 1380 |
| TCTTAAAGAT | GGTTGTTGGA | GGGATCCTTT | GGCTATTATG | GAGAACATTA TTCGTTTATC | 1440 |
| TCCAGATGTG | ATAGACAAAG | GGCTGTGTGG | CCTGTGAGAC | CGATGGCCAC TTAATTATTG | 1500 |
| GTTTTTTGTC | AATGGTTGTG | TATGCATAGA | AATTCCCACA | ACCGTTTGTG GCTTAACACA | 1560 |
| ATTTACCAGG | GGTTTAAGTG | GTTAAATTGA | TACATGTAGA | TCTAAAGTTT TATGCTAATA | 1620 |
| TAAATTAGTT | TTAATTATAT | AAATTTTAAC | TACGCTCATG | ACACGTAAAT GGTAGACCAA | 1680 |
| TATGTGGTGC | TCTATTAACT | AAGGGGTGCT | TCATTATTAA | TTCATAAAGA TTTCTTTACT | 1740 |

| | | | | | | |
|---|---|---|---|---|---|---|
| ATACAAGACT | TGTCAAAAGG | AAAAGTAGTA | TTTTCGTACT | ACGTCTACCC | CTCTCACGGA | 1800 |
| TATGTGTGGT | CGAGCAGTCA | TTATCATAAT | GTGGAATTTT | GAATTGAGCG | AGGTTTCAAA | 1860 |
| GTTCAAAACT | ATCACAACTA | GTCTTGATCA | ATTCTATATA | AGATCTGTGA | TCTTGGTTGA | 1920 |
| AGAAAAGAAT | CGTCGTAGGT | TGATATTTAA | CAAGGAATGG | CAAAGGAAGG | GGGC | 1974 |